United States Patent
Nakama (10) Patent No.: US 7,449,177 B2
(45) Date of Patent: Nov. 11, 2008

(54) REMEDY FOR PEMPHIGOID

(75) Inventor: Takekuni Nakama, Fukuoka (JP)

(73) Assignees: Asubio Pharma Co., Ltd., Tokyo (JP); Maruho Co. Ltd., Osaka (JP)

( * ) Notice: Subject to any disclaimer, the term of this patent is extended or adjusted under 35 U.S.C. 154(b) by 0 days.

(21) Appl. No.: 10/518,759

(22) PCT Filed: Dec. 26, 2003

(86) PCT No.: PCT/JP03/17031

§ 371 (c)(1), (2), (4) Date: Dec. 21, 2004

(87) PCT Pub. No.: WO2004/058295

PCT Pub. Date: Jul. 15, 2004

(65) Prior Publication Data

US 2006/0104947 A1 May 18, 2006

(30) Foreign Application Priority Data

Dec. 26, 2002 (JP) .............................. 2002-375892

(51) Int. Cl.
*A61K 38/21* (2006.01)
*A01N 37/18* (2006.01)
(52) U.S. Cl. ......................................... 424/85.5; 514/2
(58) Field of Classification Search ........................ None
See application file for complete search history.

(56) References Cited

U.S. PATENT DOCUMENTS 5,145,677 A * 9/1992 von Eichborn et al. ..... 424/85.5
5,171,567 A * 12/1992 Tara ........................... 424/85.5
2003/0053985 A1* 3/2003 Shachar et al. ............. 424/85.5

FOREIGN PATENT DOCUMENTS

| EP | 304291 | 2/1989 |
|----|--------|--------|
| EP | 845268 | 6/1998 |
| WO | WO 9527499 | 10/1995 |
| WO | WO 9527502 | 10/1995 |
| WO | WO 9606630 | 3/1996 |
| WO | WO 96/28183 | 9/1996 |

OTHER PUBLICATIONS

Fitzgerald, K.A., et al. The Cytokine Facts Book. 2001. Academic Press. 2nd Ed. p. 322-327.*
International Search Report for PCT/JP03/17031 mailed Feb. 10, 2004 (PCT/ISA/210).
Physician's Desk Reference (2003), pp. 1756-1758.

* cited by examiner

*Primary Examiner*—Robert Landsman
*Assistant Examiner*—Bruce D. Hissong
(74) *Attorney, Agent, or Firm*—Hunton & Williams LLP (57) ABSTRACT

An agent for treatment of pemphigoid is provided.

For use as an agent for treatment of pemphigoid, IFN-γ is administered in a dose of 2,000,000 JRU once daily for 7 days by intravenous drip infusion. Depending on symptoms, side effects and age of a patient, the dose can be change, or the dosage can changed to intravenous drip infusion given once in several days. IFN-γ is fast-acting against pemphigoid, involves few side effects, and is considered to be effective. The mechanism of action is presumed to be that IFN-γ suppresses the chemotaxis and function of eosinophils which are considered to be directly involved in the occurrence of pemphigoid.

7 Claims, 5 Drawing Sheets

REMEDY FOR PEMPHIGOID

CROSS REFERENCED RELATED APPLICATION

This application is a National Stage International Application No. PCT/JP03/17031, filed Dec. 26, 2003, which claimed priority to Japanese application 375892/2002, filed on Dec. 26, 2002, both of which are hereby incorporated by reference in their entirety.

TECHNICAL FIELD

This invention relates to an agent for treatment of pemphigoid, containing interferon gamma (IFN-γ) as an active ingredient.

BACKGROUND OF THE INVENTION

Pemphigoid is a skin disease classified as a type of acquired bullous dermatosis among bullous dermatoses. It is an autoimmune disease classified into bullous pemphigoid (including nodular pemphigoid), cicatricial pemphigoid (benign mucosal pemphigoid), herpes gestationis, and juvenile pemphigoid. Cicatricial pemphigoid (benign mucosal pemphigoid) is further subclassified into anti-BP180 type cicatricial pemphigoid, anti-laminin 5 type cicatricial pemphigoid, and ocular cicatricial pemphigoid.

Of these diseases, bullous pemphigoid (BP) is one of representative autoimmune bullous dermatoses in the field of dermatology. Its characteristic clinical symptoms start with edematous erythemas. Then, tense blister, large and small, develop in erythematous plaques, and only blister appear occasionally. These symptoms occur mainly in the extremities and trunk with a high incidence, rupture and form erosions. Erosions, if systemically generated, may cause bacterial infection, and losses of water and protein in the body. Thus, edemas may develop systemically, or electrolyte abnormality in the blood and dehydration may occur, resulting in a worsened generalized condition. Pruritus is frequently noted as a subjective symptom. In terms of age, BP occurs most frequently in elderly people at 70 years of age or higher, but may rarely occur in children and young persons. Histopathological findings include subepidermal blisters, and inflammatory cell infiltrations predominantly of the eosinophilic origin. The direct immunofluorescence technique shows deposition of IgG and C3 in the basement membrane zone. Visceral malignant tumor may be occasionally involved as a complication, partly because BP occurs most frequently in the elderly.

In the treatment of pemphigoid typified by BP, external use of corticosteroids has so far been performed for erythema as a dermal symptom, and external use of EKSALB® or zinc oxide ointment (unguentum simplex) has been performed for erosion. Since external use of such drugs alone has proved insufficient in efficacy, however, oral administration of tetracycline antibiotics (MINOMYCIN®, ACHROMYCIIN®), nicotinamide, and corticosteroids has been implemented for systemic administration. If these treatments are still ineffective, systemic administration of immunosuppressants or plasmapheresis has been carried out. For pruritus, antihistaminics or antiallergic drugs have been administered as symptomatic therapies.

IFN-γ, on the other hand, has been demonstrated to have various biological actions, since it was discovered as a virus proliferation inhibiting factor produced by cells. Studies aimed at its clinical applications based on these actions have been conducted to show its effectiveness against atopic dermatitis, herpesvirus infection, and cutaneous T cell lymphoma among skin diseases. However, the results of investigation of the effectiveness of IFN-γ against pemphigoid have not been reported. Nor have there been any reports of cases of its use in the clinical setting.

In treating pemphigoid, it requires a follow-up care for a long term even after it is alleviated and nearly healed, because this disease is an autoimmune disease. Usually, its treatment begins with the oral administration of tetracycline antibiotics and nicotinamide whose systemic burden is light. However, the oral administration of these drugs alone is not sufficiently effective in many patients, and the systemic administration of corticosteroids is often concomitantly used. In the systemic administration of corticosteroids, large doses are administered at the start of treatment, and often produce an excellent effect. However, hospital stay for about 2 months is required until the dose is decreased to a safety dose permitting treatment at the outpatient clinic. If the corticosteroids prove ineffective, systemic administration of immunosuppressants or plasmapheresis may be used concomitantly.

In the elderly, such treatments performed for long periods are prone to cause complications, such as hypertension, diabetes, osteoporosis, interstitial pneumonia, and bacterial infection. Once such complications occur, therapy for their symptoms may be needed to lengthen the period of hospitalization to 3 to 4 months. Furthermore, the patients may be extremely debilitated, and die of complications. Alternatively, while the doses of the administered drugs are decreased, eruptions may be aggravated. Increasing the doses again may postpone discharge from the hospital, posing difficulty with treatment.

Hence, treatment with a pharmaceutical is desired, the pharmaceutical which, when used alone, is effective, is fast-acting and involves few side effects, whose action is persistent for a long term, and which enables a corticosteroid or an immunosuppressant, if used concomitantly, to be promptly decreased in dose, even if recurrence of pemphigoid is noted during treatment with the pharmaceutical. In the presence of such a pharmaceutical, the patient would be able to leave the hospital and return to society early. In the event of recurrence, rehospitalization for a short term would be able to achieve successful treatment. Against the background of these circumstances, the present invention has, as an object, the provision of a pharmaceutical which can solve the above-described problems in the therapy of pemphigoid.

SUMMARY OF THE INVENTION

The inventor has clarified that IFN-γ shows a marked therapeutic effect on pemphigoid, thus accomplishing the present invention. That is, the present invention provides an agent for treatment of pemphigoid, which contains IFN-γ as an active ingredient. IFN-γ is fast-acting against pemphigoid, involves few side effects, and proves effective. The mechanism of action of IFN-γ is presumed to be that IFN-γ suppresses the chemotaxis and function of eosinophils which are considered to be directly involved in the onset of pemphigoid.

Pemphigoid herein refers to an autoimmune disease, including bullous pemphigoid (BP), nodular pemphigoid, cicatricial pemphigoid, juvenile pemphigoid, and other pemphigoid. Particularly, bullous pemphigoid, cicatricial pemphigoid, and nodular pemphigoid, typically, bullous pemphigoid, can be expected to be successfully treated with the agent for treatment according to the present invention. Moreover, treatment of pemphigoid is taken to have meanings, including the alleviation of symptoms of pemphigoid by administration of IFN-γ, the prevention of reaggravation of alleviated symptoms, and the suppression of incidence of symptoms in patients suspected of having initial symptoms of pemphigoid.

DETAILED DESCRIPTION OF PREFERRED EMBODIMENTS

IFN-γ used in the present invention may be that of the natural or recombinant gene type, such as IFN-γ1a (interferon gamma-1a), LFN-γ1b (interferon gamma-1b), and IFN-γn1 (interferon gamma-n1). However, IFN-γ of the recombinant gene type is preferred as a stable source of supply. For example, BIOGAMMA® which is an IFN-γ preparation marketed by Daiichi Suntory Pharma as an agent for treatment of mycosis fungoides, can be used directly. Unless the effectiveness of the present invention is lost, an IFN-γ mutant resulting from the deletion, insertion and substitution of a constituent amino acid effected in the above IFN-γ can be used, instead of this IFN-γ, with the IFN-γ mutant being adjusted such that its clinical use can be made. Examples of such an IFN-γ mutant are the IFN-γ in which 4 amino acids (Cys-Tyr-Cys-Gin) at the N-terminal have been deleted (Japanese Patent Publication No. 1995-45516), that in which an amino acid at the C-terminal has been deleted by processing (for example, a mutant described in Japanese Patent Application Laid-Open No. 1985-84298, prepared by deletion of the C-terminal 11 amino acids), and that in which the 9th amino acid has been converted from Lys to Gln (for example, Japanese Patent Publication No. 1995-45515).

The agent for treatment according to the present invention contains IFN-γ, preferably, as an intravenous preparation for drip infusion, for treatment of pemphigoid. The agent for treatment of pemphigoid according to the present invention can be administered, for example, such that 200,000 to 4,000,000 JRU of IFN-γ, once or several times daily, is administered every day or every suitable days according to symptoms, with the symptoms being observed. The dose, the administration interval, and the administration frequency can be changed, as appropriate, according to symptoms, side effects, and the patient's age.

An example of the preferred mode is the intravenous drip infusion of 2,000,000 JRU, once daily, for 7 consecutive days. After alleviation of symptoms, this dose can be administered at intervals, i.e., every 2 to 3 days, or once in 1 to 2 weeks. If a side effect due to this treatment occurs, the dosage can be changed to an intravenous drip infusion once in several days according to its symptoms. To suppress fever, one of side effects, an analgesic antipyretic drug can be used in combination. Furthermore, systemic administration of pharmaceuticals which have been used in the treatment of pemphigoid, such as corticosteroids, and the concomitant use of antihistaminics and antiallergics as symptomatic therapies are also possible. As steroid drugs, for example, prednisolone, methylprednisolone, betamethasone, and dexamethasone can be used. As antiallergics, ketotifen fumarate, olopatadine hydrochloride, cetirizine hydrochloride, ebastine, and fexofenadine hydrochloride can be used. As antihistaminics, homochlorcyclizine hydrochloride, chlorpheniramine maleate, mequitazine, clemastine fumarate, and cyproheptadine hydrochloride can be used. However, these drugs are not restrictive, and the steroid drugs, antiallergics, and antihistaminics usually used in the field of dermatology can all be used. These drugs may be incorporated, together with IFN-γ, into the pharmaceutical preparation of the present invention, or may be used concomitantly as separate drugs.

The pharmaceutical preparation of the present invention may contain carriers, adjuvants, and additives, which are customarily used for the production of pharmaceuticals, in addition to IFN-γ. For example, IFN-γ can be prepared into pharmaceutical preparations, such as intravenous injections, by publicly known pharmaceutical manufacturing methods using those agents, including tonicity agents, such as sodium chloride and potassium chloride; buffering agents, such as sodium hydrogenphosphate, and sodium dihydrogenphosphate; stabilizers, such as sodium edetate; antiseptics, such as ethylparaben, butylparaben, and benzalkonium chloride; and pH adjustors, such as sodium hydroxide and dilute hydrochloric acid. IFN-γ preparations can be produced, for example, by adding suitable stabilizers and buffering agents to a purified IFN-γ stock solution, and lyophilizing the mixture.

The effect of treating pemphigoid by the agent for treatment, which contains IFN-γ, according to the present invention is evaluated by the efficacy evaluation method performed in daily medical care, which uses amelioration of dermal symptoms, etc. In the case of bullous pemphigoid, for example, three symptoms in the patient, i.e., erythemas, blister and erosions, are used as indicators, and the severity of these symptoms, before, during and after treatment with the therapeutic agent of the present invention, is evaluated on a scale of 5 grades, whereby the efficacy of the agent for treatment according to the present invention can be evaluated. For example, erythemas, blister and erosions are evaluated by the 5-grade system described below. If a favorable change occurs in at least one of these indicators, it is determined that the symptoms of the patient with pemphigoid has been alleviated.

1) Erythemas

0: No erythemas. Almost all of lesions are pigmentations.
1: Erythemas account for less than ⅓ of all lesions. The remainder are pigmentations.
2: Erythemas account for ⅓ to ⅔ of all lesions. The remainder are pigmentations.
3: Unchanged.
4: Erythemas expand and newly develop.

2) Blister

-continued

0: No bullae.
1: Less than ⅓ of the number of blister present at admission to hospital.
2: ⅓ to ⅔ of the number of blister present at admission to hospital.
3: No change in the number of blister.
4: Blister newly develop.

3) Erosions

0: No erosions. Nearly all lesions are epithelialized.
1: Erosions are less than ⅓ of erosions present at admission to hospital. The remainder are epithelialized.
2: Erosions are ⅓ to ⅔ of erosions present at admission to hospital. The remainder are epithelialized.
3: No change in the area of erosions.
4: Erosions tend to expand.

[Actions]

The mechanism of action of IFN-γ, namely, how IFN-γ works effectively in the treatment of pemphigoid, has not yet been accurately elucidated, like the mechanism of onset of pemphigoid which has remained still unknown. Pemphigoid is an autoimmune disease, and involves peripheral blood eosinophilia and marked eosinophilic infiltration into tissues. The inventor and others previously conducted immunohistological studies and electron microscopic morphological studies of eosinophils infiltrating into tissues of patients with pemphigoid, and reported that eosinophils were involved in the generation of BP[1)2)]. They also clarified that in the peripheral blood eosinophils of patients with pemphigoid, density heterogeneity of eosinophils existed, and hypodense active eosinophils significantly increased[3)], and that ECP concentration in a BP bullous liquid was markedly high[4)]. BP is an autoimmune disease, and it is speculated that pemphigoid can be treated by suppressing the infiltration and function of eosinophils which may be fully involved in the occurrence of BP, as described above.

There are many factors which differentiate, induce and activate eosinophils. It has been elucidated, in particular, that cytokines, such as IL-3, IL-5 and GM-CSF, are mainly involved as factors acting on hematopoietic stem cells of the bone marrow to the peripheral blood. Normally, helper T cells of peripheral blood T cells are classified into Th1 cells and Th2 cells by the type of cytokines produced by the helper T cells, and the above-mentioned IL-3, IL-5 and GM-CSF are produced by Th2 cells. In the normal state, there is a balance between these two types of cells, such that Th2 cells are suppressed via IFN-γ produced by Th1 cells, and Th1 cells are suppressed by IL-10 produced by Th2 cells.

Since Th2 cells are dominant, IL-3, IL-5 and GM-CSF may partake in eosinophilic leukocytosis and eosinophilic infiltration concerned with the pathogenesis of pemphigoid. Thus, it is assumed that the administration of IFN-γ will suppress the function of Th2 cells to suppress the production of IL-3, IL-5 and GM-CSF, thereby suppressing the differentiation, induction and activation of eosinophils, thus eventually leading to the alleviation of symptoms of pemphigoid.

EXAMPLES

Cases in which IFN-γ produced an excellent response in BP patients intractable to various therapies will be explained by way of Examples.

[Clinical Case 1] Example (1) of Treatment with IFN-γ in BP Patient

Subject: A 58-year-old male.
Chief complaints: Systemic edematous erythemas, blister, erosions.
Family history: Nothing of note.
Past history: Schizophrenia and epilepsy since 1992.
Present illness and course: Tense blister frequently occurred at the upper extremities and back since February 2001. Upon scrutiny at Kurume University Hospital, a diagnosis of BP was made. The oral administration of Achromycin (registered trademark) and nicotinamide was begun, but because of aggravation, concomitant use of prednisolone, 30 mg p.o., was initiated. The symptoms were alleviated transiently, but when the dose of prednisolone was decreased to 15 mg, the symptoms were recrudescent. Thus, the dose of prednisolone was increased to 30 mg, but blister developed newly, necessitating admission to the hospital in January 2002. After admission, plasmapheresis was performed a total of 13 times, and the steroid administered orally was changed from 3 mg betamethasone to 50 mg prednisolone. As the symptoms were alleviated, the dose of prednisolone was decreased from 40 mg to 20 mg to 15 mg, and the patient was discharged from the hospital in April 2002. Then, the course of the patient's condition was followed up at the outpatient department over 15 mg prednisolone, 100 mg minocycline, and 900 mg nicotinamide. One month after discharge from the hospital, large and small bullae systemically occurred again at multiple sites, and thus the patient was admitted again to the hospital in May 2002. After admission, many bullae and erosions were observed systemically, but the doses of prednisolone, minocycline and nicotinamide were not increased. Instead, the administration of IFN-γ, 2,000,000 JRU (1V) once daily for consecutive days by i.v. drip infusion, was begun on May 24. However, an epileptic attack occurred on May 26, necessitating discontinuation of IFN-γ treatment. Because of the past history, IFN-γ treatment on alternate days was cautiously resumed on May 29, and 7V was completed by June 4. Since an excellent response was obtained, 1V was given once in 3 to 4 days thereafter. In August, intravenous drip infusion was performed once weekly without recurrence. Currently, the patient's course is satisfactory through drip infusion performed once biweekly at the outpatient department. In regard to oral administration, minocycline and nicotinamide were discontinued, and prednisolone is continued only in a dose of 5 mg, but prednisolone is to be discontinued sometime. Epilepsy was observed only once, and not seen thereafter. Thus, its relation with IFN-γ was negated. Fever after administration of IFN-γ was observed in the 38° C. to the 39° C. range until the fourth administration, but thereafter changed to slight fever in the 37° C. range. Currently, no antipyretic is used.

Figure 1:
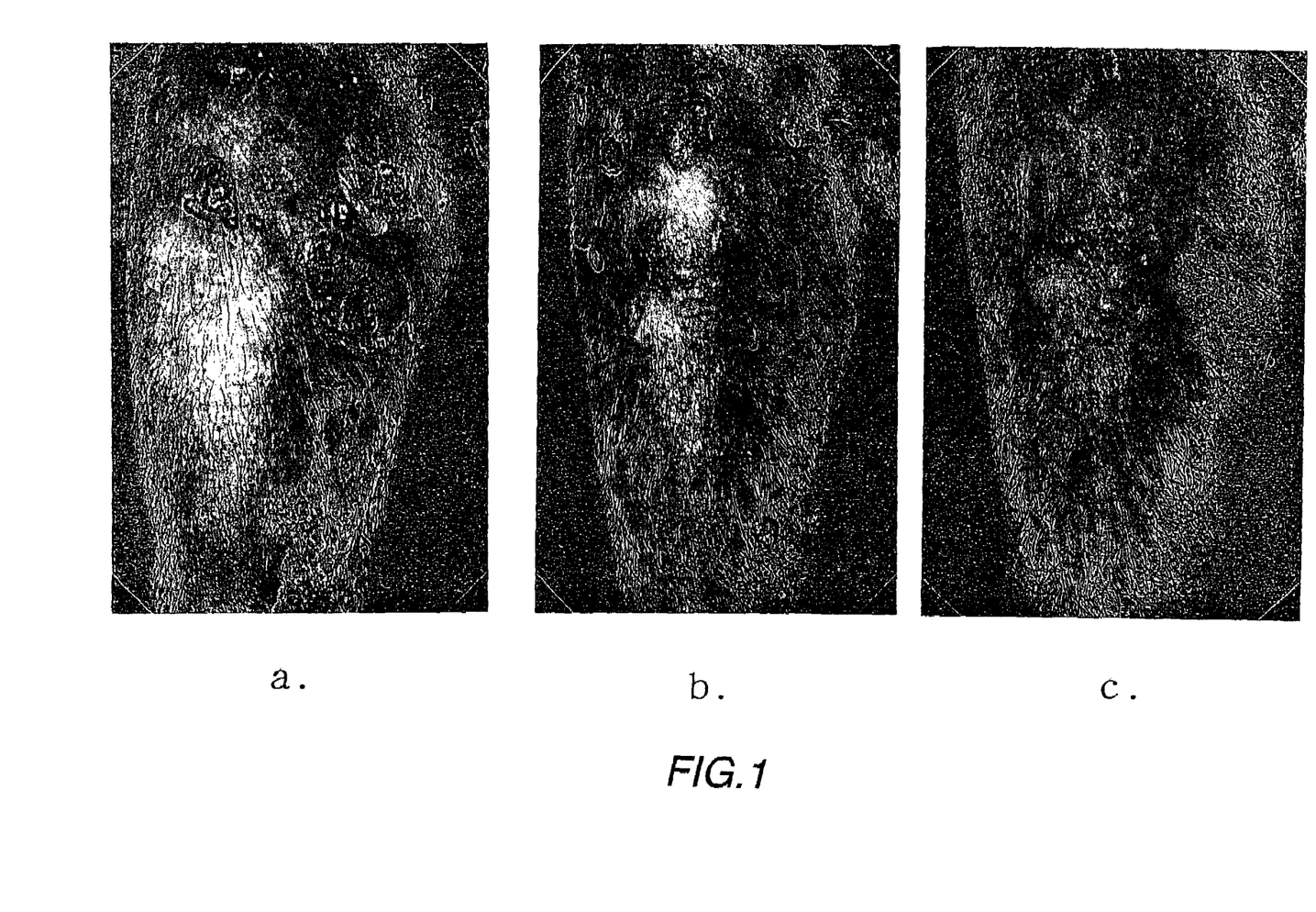
FIGS. 1a to 1c are clinical course photographs (right thigh) of Case 1, FIG. 1a showing a clinical image before treatment with IFN-γ, FIG. 1b showing a clinical image after 2 days of IFN-γ treatment, and FIG. 1c showing a clinical image after completion of 7V.

Before IFN-γ treatment (May 23), blister and erosions developed systemically at multiple sites (FIG. 1a). After 2 days of treatment (May 26), the symptoms were considerably relieved (FIG. 1b). At completion of 7V (June 5), no blister newly occurred, and further alleviation was observed (FIG. 1c). At present, all lesions are pigmentations, and none of erythemas, blister and erosions are seen. The evaluations were 2 (May 26)→1 (June 5)→0 (August 22) for erythemas, 1 (May 26)→0 (June 5)→0 (August 22) for blister, and 2 (May 26)→1 (June 5)→0 (August 22) for erosions, as shown in Table 1.

The peripheral blood eosinophil count decreased as follows: 1190 (May 23)→1246 (May 27)→602 (June 4)→356 (September 4). The blood IL-3, IL-4, IL-5 and GM-CSF levels all showed low values before and after IFN-γ treatment.

TABLE 1

| Day of examination | May 26 | June 5 | August 22 |
| --- | --- | --- | --- |
| Erythemas | 2 | 1 | 0 |
| Blister | 1 | 0 | 0 |
| Erosions | 2 | 1 | 0 |

[Clinical Case 2] Example (2) of Treatment with IFN-γ in BP Patient

Subject: A 74-year-old male.

Chief complaints: Edematous erythemas and blister of the extremities and trunk.

Family history: Nothing of note.

Past history: Cerebral infarction in 1992.

Present illness and course: Erythemas accompanied by pruritus occurred frequently in April 2002. External application of a corticosteroid, and the oral administration of celestamine were prescribed by a local doctor, but erythemas with blister began to appear. Thus, the patient was referred to Kurume University Hospital. Upon close examination, a diagnosis of BP was made, and the oral administration of 300 mg roxithromycin, 1,500 mg nicotinamide, and 20 mg prednisolone was started on May 8. Since the symptoms were not alleviated, however, the patient was admitted to the hospital on May 17. The oral administration of these drugs was continued in the same doses, but new occurrence of blister was observed. Thus, the administration of IFN-γ, 2,000,000 JRU (1V) once daily by i.v. drip infusion, was begun on June 15. Following this treatment for 7 consecutive days, an excellent response was obtained, and then IFN-γ treatment was changed to i.v. drip infusion performed once in 3 days. The dose of prednisolone was also decreased to 12.5 mg, beginning on June 22, and further decreased to 10 mg from July 8. Since no recurrence was observed thereafter, the patient was given IFN-γ once weekly, and discharged from the hospital on August 7. Currently, the dose of prednisolone is 5 mg, and IFN-γ is administered once biweekly by drip infusion, with no recurrence seen.

Figure 2:
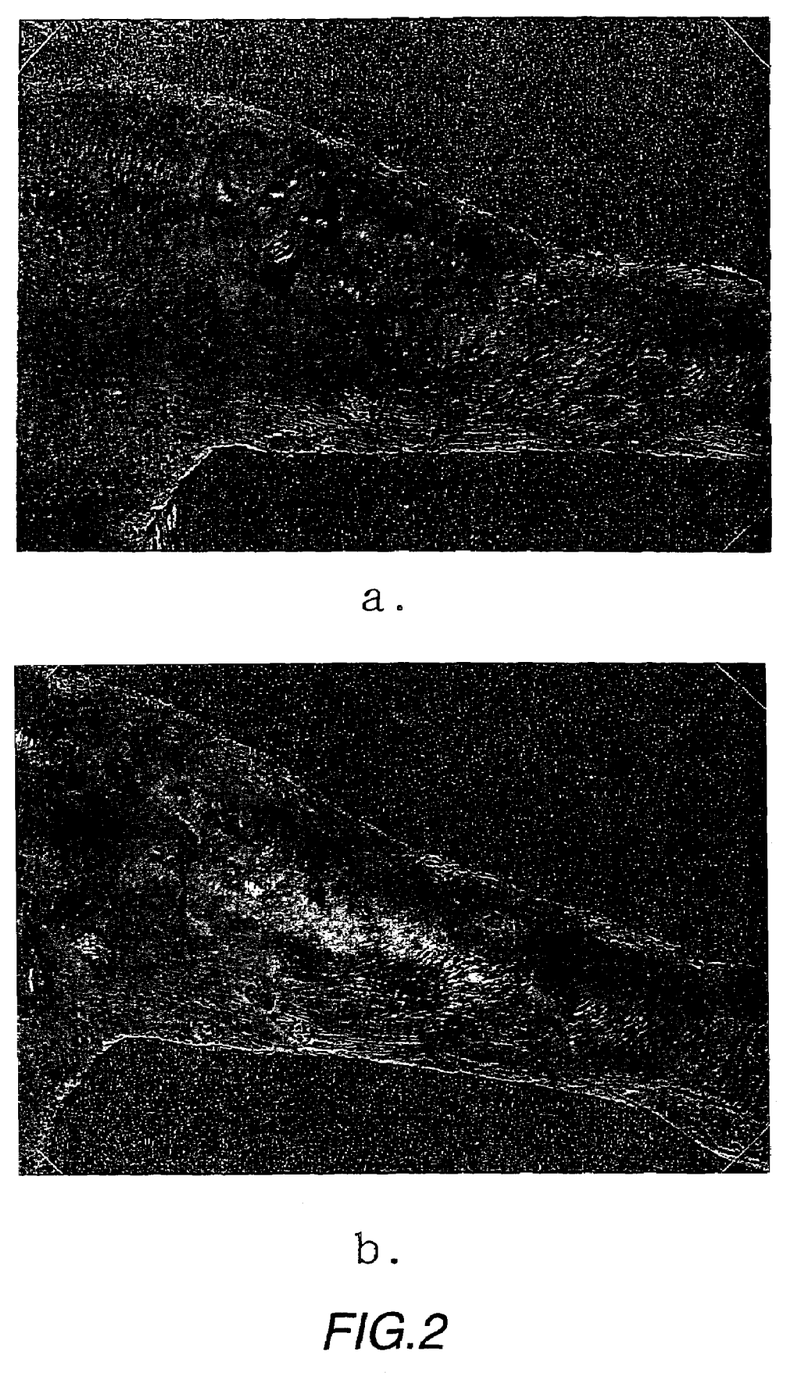
FIGS. 2a and 2b are clinical course photographs of Case 2, FIG. 2a showing a clinical image before treatment with IFN-γ, and FIG. 2b showing a clinical image after completion of 7V.

Before IFN-γ treatment (June 14), erythemas, blister and erosions developed systemically at multiple sites (FIG. 2a). At completion of 7V (June 21), all the blister disappeared, and nearly all of the erosions were epithelialized (FIG. 2b). The evaluations were 1 (June 17)→0 (June 21) for erythemas, 1 (June 17)→0 (June 21) for blister, and 1 (June 17)→0 (June 21) for erosions, as shown in Table 2. Still now, no recurrence of eruptions is noted.

The peripheral blood eosinophil count decreased as follows: 2619 (June 13)→1136 (June 18)→1218 (June 21)→143 (September 25). The blood IL-3 and GM-CSF levels both showed low values before and after IFN-γ treatment. On the other hand, blood IL-5 and IL-4 were decreased following treatment; IL-5 was 18.5 pg/ml before treatment, and 5.0 pg/ml or less after treatment, and IL-4 was 15.6 pg/ml before treatment, and 4.6 pg/ml after treatment.

TABLE 2

| Day of examination | June 17 | June 21 |
| --- | --- | --- |
| Erythemas | 1 | 0 |
| Blister | 1 | 0 |
| Erosions | 1 | 0 |

[Clinical Case 3] Example (3) of Treatment with IFN-γ in BP Patient

Subject: A 67-year-old female.

Chief complaints: Systemic edematous erythemas, blister and erosions.

Family history: Nothing of note.

Past history: Nothing particular to mention.

Present illness and course: IFN-γ, 2,000,000 JRU (1V), was administered by i.v. drip infusion on August 26, but urinary tract infection was identified, thus requiring its discontinuation. Then, IFN-γ, 2,000,000 JRU (1V), was administered once daily by i.v. drip infusion consecutively from September 10 to September 16.

Figure 3:
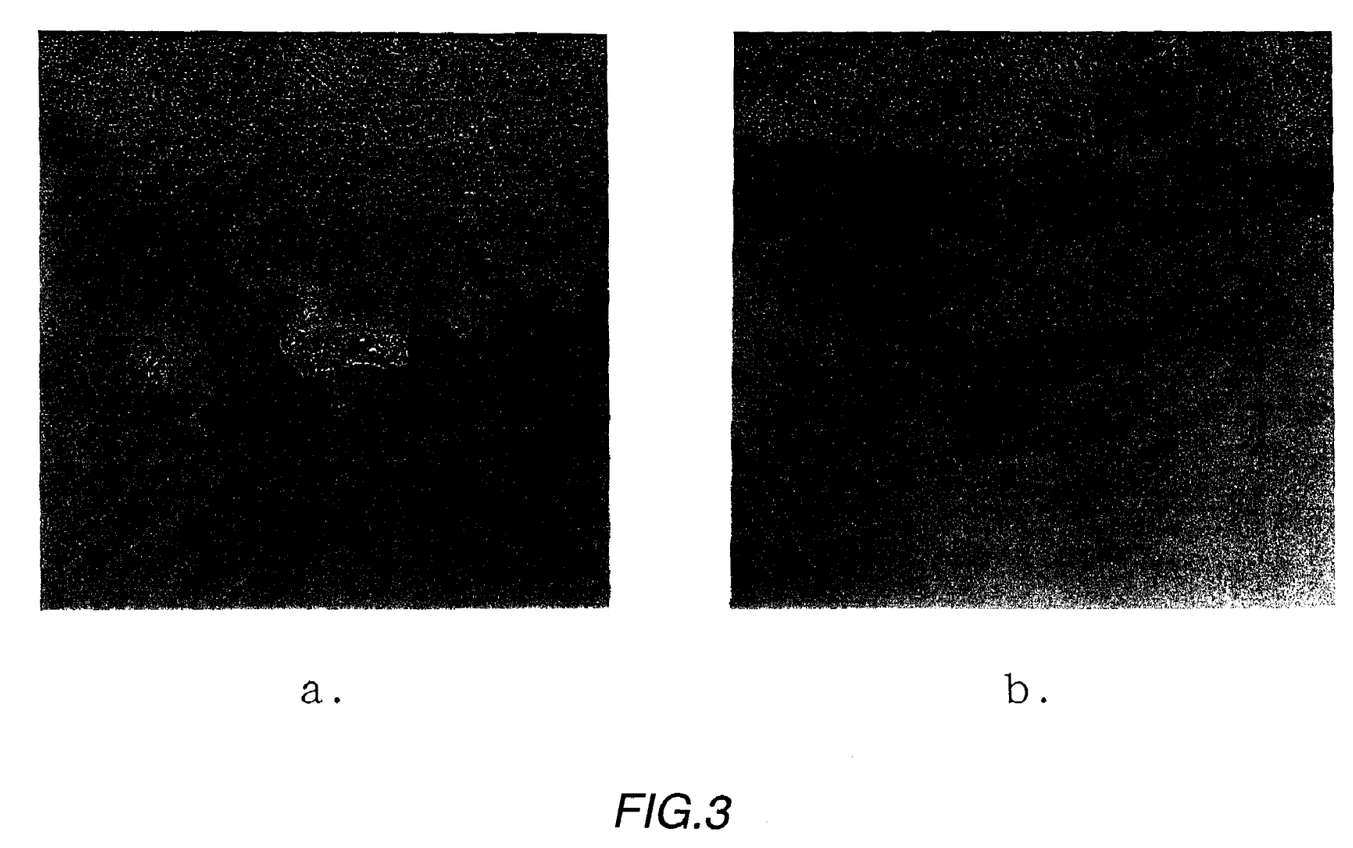
FIGS. 3a and 3b are clinical course photographs (chest) of Case 3, FIG. 3a showing a clinical image before treatment with IFN-γ, and FIG. 2b showing a clinical image after treatment.

Before IFN-γ treatment (August 26), erythemas, blister and erosions developed systemically at multiple sites (FIG. 3a). After treatment (September 17), the symptoms were considerably relieved, and no blister developed newly (FIG. 3b). Currently, all the affected sites show only pigmentations, and none of erythemas, blister and erosions are observed. The evaluations were 2 (September 13)→1 (September 17) for erythemas, 2 (September 13)→0 (September 17) for blister, and 2 (September 13)→1 (September 17) for erosions, as shown in Table 3.

The peripheral blood eosinophil count decreased as follows: 288 (August 26)→310 (September 2)→39 (September 13)→0 (September 17). The blood IL-3, IL-5 and GM-CSF levels all showed low values before and after IFN-γ treatment (August 26, September 17). On the other hand, blood IL-4 was slightly decreased: 16.8 pg/ml before treatment (August 26), and 12.7 pg/ml after treatment (September 17).

TABLE 3

| Day of examination | September 13 | September 17 |
| --- | --- | --- |
| Erythemas | 2 | 1 |
| Blister | 2 | 0 |
| Erosions | 2 | 1 |

[Clinical Case 4] Example (4) of Treatment with IFN-γ in BP Patient

Subject: A 68-year-old female.

Chief complaints: Systemic edematous erythemas, blister and erosions.

Family history: Nothing of note.

Past history: Nothing particular to mention.

Present illness and course: IFN-γ, 2,000,000 JRU (1V), was administered once daily consecutively from January 21 to January 27 by intravenous drip infusion.

Before IFN-γ treatment (January 21), erythemas, blister and erosions developed systemically at multiple sites. After treatment (January 28), the symptoms were considerably relieved, and no blister developed newly. After one week of treatment (February 5), only pigmentations were observed, and none of erythemas, bullae and erosions were observed.

The evaluations were 2 (January 24)→1 (January 28)→0 (February 5) for erythemas, 2 (January 24)→0 (January 28)→0 (February 5) for blister, and 2 (January 24)→1 (January 28)→0 (February 5) for erosions, as shown in Table 4.

The peripheral blood eosinophil count decreased as follows: 5334 (January 21)→5202 (January 24)→5251 (January 28)→2736 (January 31)→0 (February 5). The blood IL-3, IL-4, and GM-CSF levels all showed low values before and after IFN-γ treatment (January 21, January 28). On the other hand, blood IL-5 was decreased: 76.1 pg/ml before treatment (January 21), and 28.3 pg/ml after treatment (January 28).

TABLE 4

| Day of examination | January 24 | January 28 | February 5 |
| --- | --- | --- | --- |
| Erythemas | 2 | 1 | 0 |
| Blister | 2 | 0 | 0 |
| Erosions | 2 | 1 | 0 |

[Clinical Case 5] Example (5) of Treatment with IFN-γ in BP Patient

Subject: A 93-year-old male.
Chief complaints: Systemic edematous erythemas, blister and erosions.
Family history: Nothing of note.
Past history: Diabetes, hypertension.
Present illness and course: IFN-γ, 2,000,000 JRU (1V), was administered once daily consecutively from June 6 to June 12 by intravenous drip infusion.

Before IFN-γ treatment (June 6), erythemas, blister and erosions developed systemically at multiple sites. After treatment (June 12), the symptoms were considerably relieved, and no blister developed newly. After one week of treatment (June 19), only pigmentations were observed, and none of erythemas, blister and erosions were observed. The evaluations were 3 (June 9)→2 (June 12)→1 (June 19) for erythemas, 2 (June 9)→0 (June 12)→0 (June 19) for blister, and 2 (June 9)→1 (June 12)→0 (June 19) for erosions, as shown in Table 5.

The peripheral blood eosinophil count decreased as follows: 1080 (May 29)→190 (June 6)→71 (June 9)→54 (June 12)→0 (June 19). The blood IL-3 and GM-CSF levels all showed low values before and after IFN-γ treatment (June 6, June 12). On the other hand, blood IL-4 and IL-5 were decreased; IL-4 was 7.5 pg/ml before treatment (June 6), and 4.0 pg/ml after treatment (June 12), and IL-5 was 7.5 pg/ml before treatment (June 6), and less than 5.0 pg/ml after treatment (June 12).

TABLE 5

| Day of examination | June 9 | June 12 | June 19 |
| --- | --- | --- | --- |
| Erythemas | 3 | 2 | 1 |
| Blister | 2 | 0 | 0 |
| Erosions | 2 | 1 | 0 |

[Clinical Case 6] Example (6) of Treatment with IFN-γ in BP Patient

Subject: A 55-year-old male.
Chief complaints: Systemic edematous erythemas, blister and erosions.
Family history: Nothing of note.
Past history: Nothing particular to mention.
Present illness and course: IFN-γ, 2,000,000 JRU (1V), was administered once daily consecutively from August 26 to September 1 by intravenous drip infusion.

Figure 4:
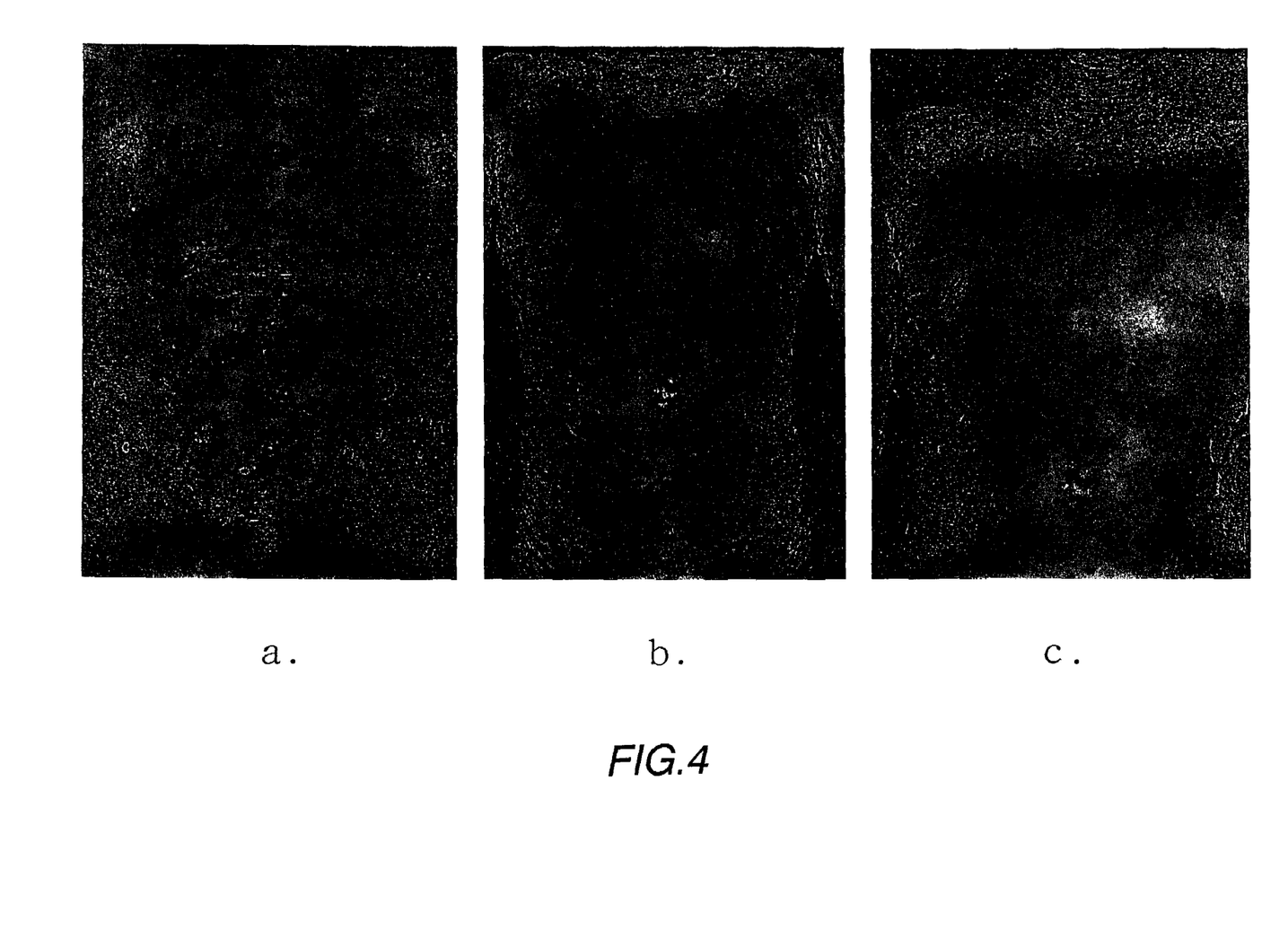
FIGS. 4a to 4c are clinical course photographs (abdomen) of Case 6, FIG. 4a showing a clinical image before treatment with IFN-γ, FIG. 4b showing a clinical image after 3 days of treatment with IFN-γ, and FIG. 4c showing a clinical image after completion of 7V.
Figure 5:
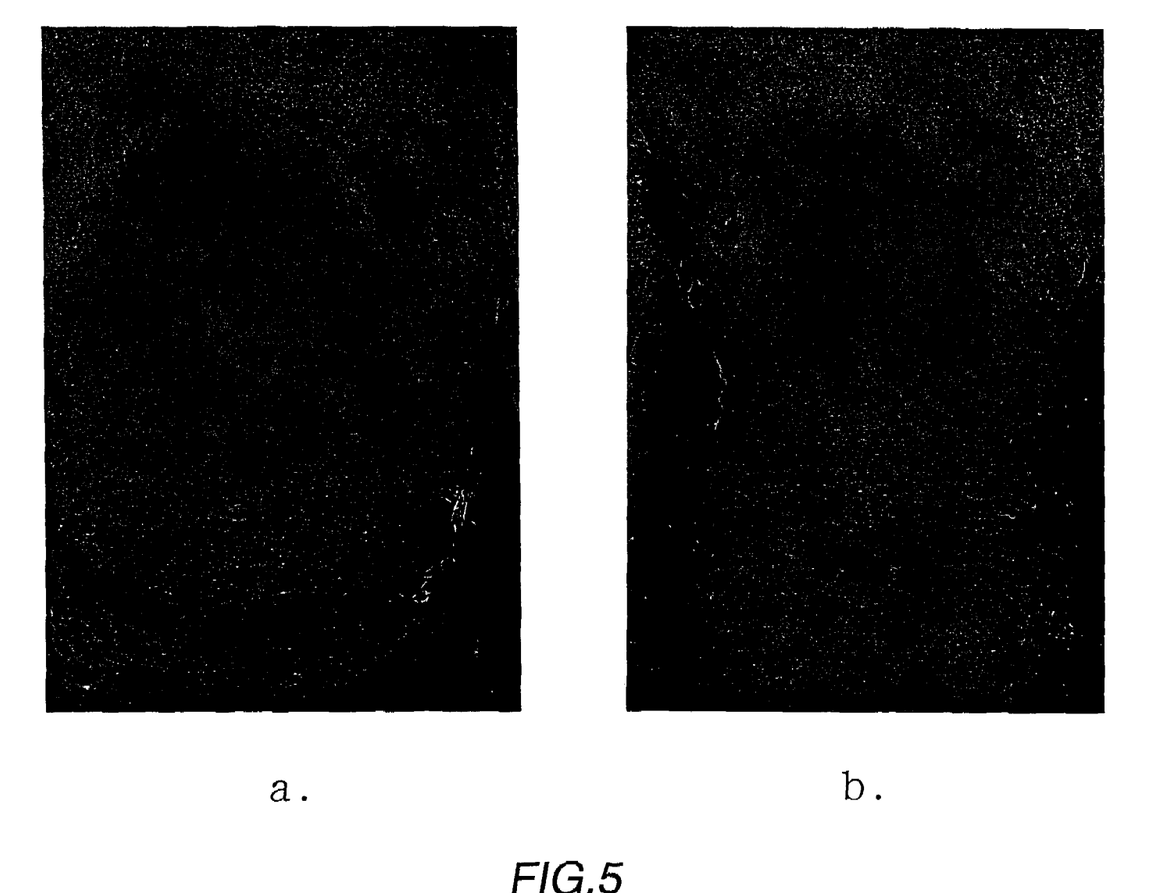
FIGS. 5a and 5b are clinical course photographs (back) of Case 6, FIG. 5a showing a clinical image before treatment with IFN-γ, and FIG. 5b showing a clinical image after completion of 7V.

Before IFN-γ treatment (August 26), erythemas, blister and erosions developed systemically at multiple sites (FIG. 4a, FIG. 5a). After treatment (September 1), the symptoms were considerably relieved, and no blister developed newly (FIG. 4b, FIG. 4c, FIG. 5c). After 10 days of treatment (September 11), only pigmentations were observed, and none of erythemas, blister and erosions were observed. The evaluations were 3 (August 28)→1 (September 1)→0 (September 11) for erythemas, 2 (August 28)→0 (September 1)→0 (September 11) for blister, and 2 (August 28)→1 (September 1)→0 (September 11) for erosions, as shown in Table 6.

The peripheral blood eosinophil count decreased as follows: 481 (August 26)→148 (August 28)→192 (September 1)→86 (September 5)→0 (September 11). The blood IL-3, IL-5 and GM-CSF levels all showed low values before and after IFN-γ treatment (August 26, September 1). On the other hand, blood IL-4 was decreased; 24.8 pg/ml before treatment (August 26), and 17.2 pg/ml after treatment (September 1).

TABLE 6

| Day of examination | August 28 | September 1 | September 11 |
| --- | --- | --- | --- |
| Erythemas | 3 | 1 | 0 |
| Blister | 2 | 0 | 0 |
| Erosions | 2 | 1 | 0 |

EFFECT OF THE INVENTION

The above results show that IFN-γ was excellently effective against pemphigoid, an intractable disease, in all cases. Following IFN-γ treatment, the eosinophil count was clearly decreased simultaneously with the alleviation of clinical symptoms. IFN-γ was thus considered to suppress Th2 cells, thereby suppressing the chemotaxis and function of eosinophils and ameliorating the symptoms. According to similar concepts, IFN-γ was reported to be administered in skin diseases, including eosinophilic pustular folliculitis (EPF)[5] and atopic dermatitis (AD)[6]. In EPF, however, other drugs produce a marked response without presenting such clinical symptoms as to affect general condition. In AD, IFN-γ is slightly effective in an acute phase, but often fails to take effect in a chronic phase. In the case of pemphigoid, the elderly are affected most frequently, and the progression of symptoms may exert influence on the general condition. Moreover, treatment extends over a long period, and side effects often develop. The present invention has made it possible to provide a method of treatment for pemphigoid for which there have been no fast-acting safe therapies.

REFERENCES

1) Takekuni NAKAMA, Shingo TSUDA, et al.: Immunohistochemical study of eosinophils using mouse anti-human ECP monoclonal antibodies (EG2). J. of Clin. & Experimental Medicine 150:231-232, 1989.
2) Takekuni NAKAMA, Shingo TSUDA: Ultrastructural and immunocytechemical aspects of infiltrated eosinophils in bullous pemphigoid. Electron Microscopy in Dermatology:181-185, 1994.
3) Shingo TSUDA, Minoru MIYASATO, et al.: Eosinophil phenotypes in bullous pemphigoid. Journal of Dermatology 19:270-279, 1992.

4) Shingo TSUDA, Minoru MIYASATO, Takekuni NAKAMA, et al.: Skin disease and eosinophils II. Hydroa. Eosinophilic infiltration and its surroundings in skin: 151-176, J. Clin. Therapeutics & Medicines, 1990.
5) M Fushimi, Y Tokura, et al.: Eosinophilic pustular folliculitis effectively treated with recombinant interferon-γ: suppression of mRNA expression of interleukin 5 in peripheral blood mononuclear cells. Br. J. Dermatology 134:766-772, 1996.
6) Seth R. Stevens, MD; Jon M. Hanifin, et al.: Long-term Effectiveness and Safety of Recombinant Human Interferon Gamma Therapy for Atopic Dermatitis Despite Unchanged Serum IgE Levels. Arch. Dermatol. 134:799-804, 1998.

The invention claimed is:

1. A method for treating bullous pemphigoid comprising administering to a human patient in need of such treatment human interferon-γ intravenously in a daily dose of 2,000,000-4,000,000 Japanese Reference Units (JRU).

2. The method according to claim 1, wherein said daily dose is 2,000,000 JRU.

3. The method according to claim 1, comprising administering human interferon-γ in combination with an antihistaminic, an antiallergic, a corticosteroid, or any combination thereof.

4. The method of claim 3, comprising administering human interferon-γ in combination with an antihistaminic.

5. The method of claim 3, comprising administering human interferon-γ in combination with an antiallergic.

6. The method of claim 3, comprising administering human interferon-γ in combination with a corticosteroid.

7. The method of claim 1, wherein said human interferon-γ is administered for seven consecutive days.

* * * * *